United States Patent
Wu et al.

(10) Patent No.: US 7,629,293 B2
(45) Date of Patent: Dec. 8, 2009

(54) MANUFACTURING METHOD OF BAMBOO CHARCOAL SUPPORTING SILVER AND PRODUCTS THEREOF

(75) Inventors: Kuo-Hui Wu, Dasi Township (TW); Fu-Chu Yang, Dasi Township (TW); Wen-Po Lin, Taipei (TW); Ming-Kuan Hu, Taipei (TW)

(73) Assignee: National Defense University, Taoyuan County (TW)

( * ) Notice: Subject to any disclaimer, the term of this patent is extended or adjusted under 35 U.S.C. 154(b) by 406 days.

(21) Appl. No.: 11/734,374

(22) Filed: Apr. 12, 2007

(65) Prior Publication Data

US 2008/0254980 A1    Oct. 16, 2008

(51) Int. Cl.
*C01B 31/08* (2006.01)
*B01J 20/22* (2006.01)
*A61K 8/02* (2006.01)
*A61K 8/18* (2006.01)
*A61K 31/74* (2006.01)
*A61K 35/00* (2006.01)
*A61K 33/08* (2006.01)
*B32B 9/00* (2006.01)
*C04B 16/02* (2006.01)
*C09C 1/44* (2006.01)

(52) U.S. Cl. .................. 502/417; 502/401; 424/401; 424/69; 424/78.05; 424/118; 424/688; 428/688; 106/406; 106/474

(58) Field of Classification Search .................. None
See application file for complete search history.

(56) References Cited

U.S. PATENT DOCUMENTS 2,424,083 A * 7/1947 Finch et al. ............. 502/347
6,509,294 B1 * 1/2003 Tatsumi .................. 502/401

FOREIGN PATENT DOCUMENTS

WO    WO 2006015317 A2 *   2/2006

OTHER PUBLICATIONS

Li et al.; Antibacterial Pitch-Based Activated Carbon Fiber Supporting Silver; Carbon; vol. 36 pp. 61-65; 1998.*

* cited by examiner

*Primary Examiner*—Melvin C Mayes
*Assistant Examiner*—Guinever S Gregorio
(74) *Attorney, Agent, or Firm*—C. G. Mersereau; Nikolai & Mersereau, P.A.

(57) ABSTRACT

The BC powders (particle size<10 μm, Taiwan Paiho) are activated with surfactant sodium alginate under stirred for 1 h. The as-prepared BC powders (2 g) are immersed into 100 mL of biamminesilver nitrate ($[Ag(NH_3)_2]NO_3$) solutions, which are formed by adding 28 wt. % aqueous ammonia into $AgNO_3$ solution at room temperature. After stirring for 1 h, dilute aqueous solutions of hydrazine monohydrate are separately prepared and introduced to the $BC-AgNO_3$ solutions in appropriate quantities (molar ratio 1:1 with respect to silver nitrate) by a syringe. Stirring is continued under inert atmosphere at room temperature for another 4 h. The BC/Ag particles are separated and washed with deionized water and ethanol, then dried in vacuum at 60° C. for overnight.

4 Claims, 9 Drawing Sheets

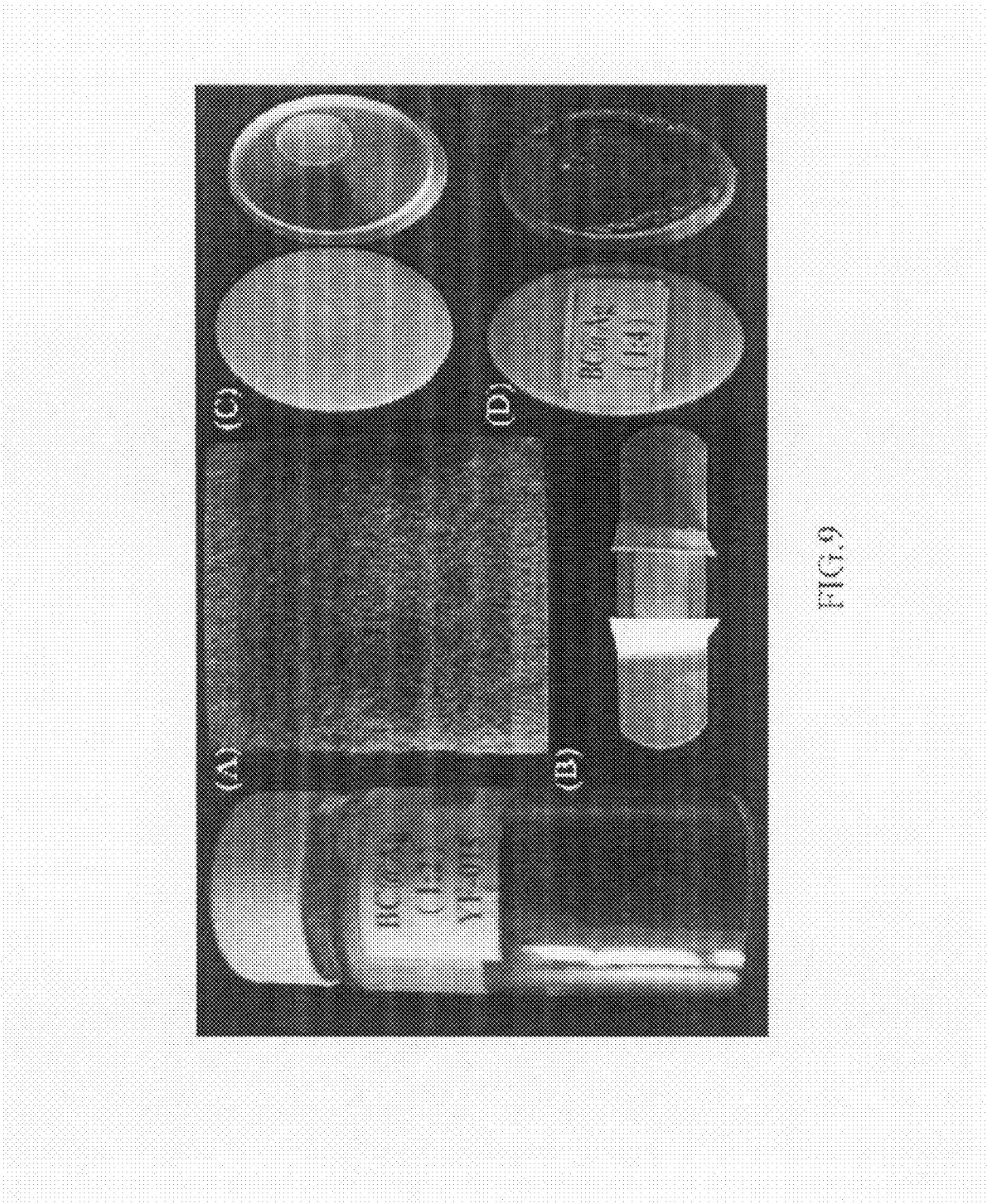

MANUFACTURING METHOD OF BAMBOO CHARCOAL SUPPORTING SILVER AND PRODUCTS THEREOF

BACKGROUND OF THE INVENTION

1. Field of the Invention

The present invention relates to a manufacturing method of bamboo charcoal (BC) supporting silver that is environmental friendly and innocent to human and has excellent antibacterial efficiency. Moreover, products generated by the manufacturing method are also disclosed.

2. Description of Related Art

Present antibacterial materials are mostly organic ones but can not last their antibacterial efficiency long. However, a silver-supported inorganic material enables to overcome this drawback. Up to now, zeolite, calcium[0] phosphate and carbon fiber have been developed as Inorganic supports for antibacterial silver-containing materials[0]. Especially, silver-supported silica materials, such as silica glass and silica thin films, are expected to be good candidates for antibacterial materials due to their fine chemical durability and high antibacterial activity. However, the inorganic antibacterial materials are not decomposed easily and thus not environmental friendly.

SUMMARY OF THE INVENTION

To overcome the foregoing drawback of the inorganic antibacterial materials, a manufacturing method for producing organic BC supporting silver (BC/Ag) and the relative products there of are provided.

A main objective of the present invention is to provide a manufacturing method of BC/Ag that produces BC/Ag composites.

The purposes of the present work are to prepare antibacterial BC/Ag using a chemical reduction method and to examine surface structures and chemistry before and after supporting silver.

To achieve the foregoing objectives, the manufacturing method comprises steps of:

The BC powders (particle size<10 μm, Taiwan Paiho) were activated with surfactant sodium alginate under stirred for 1 h. The as-prepared BC powders (2 g) were immersed into 100 mL of biamminesilver nitrate ($[Ag(NH_3)_2]NO_3$) solutions, which were formed by adding 28 wt. % aqueous ammonia into $AgNO_3$ solution at room temperature. The weight ratio between BC and $AgNO_3$ approximately equal to 1:1, 1:2, 1:3, 1:4, 1:5 and 1:6, respectively.

After stirring for 1 h, dilute aqueous solutions of hydrazine monohydrate were separately prepared and were introduced to the BC-$AgNO_3$ solutions in appropriate quantities (molar ratio 1:1 with respect to silver nitrate) by a syringe. The samples were designated in different weight ratio of 26% (BC/Ag-1) 29% (BC/Ag-2), 34% (BC/Ag-3), 48% (BC/Ag-4), 57% (BC/Ag-5), or 75% (BC/Ag-6), respectively.

By providing the bamboo charcoal combined with the silver, the BC/Ag particles have excellent antibacterial efficiency. Further benefits and advantages of the present invention will become apparent after a careful reading of the detailed description with appropriate reference to the accompanying drawings.

BRIEF DESCRIPTION OF THE DRAWINGS

FIG. 9 details several applications, BC/Ag composites applied to personal sanitary bag (9A), OK bandage (9B), tablets to purify and sterilize water (9C) and ointments for wounds (9D).

DETAILED DESCRIPTION OF THE PREFERRED EMBODIMENT

A manufacturing method of BC/Ag in accordance with the present invention comprises steps of The BC powders (particle size<10 μm, Taiwan Paiho) were activated with surfactant sodium alginate under stirred for 1 h. The as-prepared BC powders (2 g) were immersed into 100 mL of biamminesilver nitrate ($[Ag(NH_3)_2]NO_3$) solutions, which were formed by adding 28 wt. % aqueous ammonia into $AgNO_3$ solution at room temperature. The weight ratio between BC and $AgNO_3$ approximately equal to 1:1, 1:2, 1:3, 1:4, 1:5 and 1:6, respectively. After stirring for 1 h, dilute aqueous solutions of hydrazine monohydrate were separately prepared and were introduced to the BC-$AgNO_3$ solutions in appropriate quantities (molar ratio 1:1 with respect to silver nitrate) by a syringe. The color of the solutions changed to either gray or gray black due to reduction of $Ag^+$ to $Ag^0$. The samples were designated BC/Ag-1, BC/Ag-2, BC/Ag-3, BC/Ag-4, BC/Ag-5 and BC/Ag-6, respectively. Stirring was continued under inert atmosphere at room temperature for another 4 h. The BC/Ag particles were separated and washed with deionized water and ethanol, then dried in vacuum at 60° C. for overnight.

Figure 1:
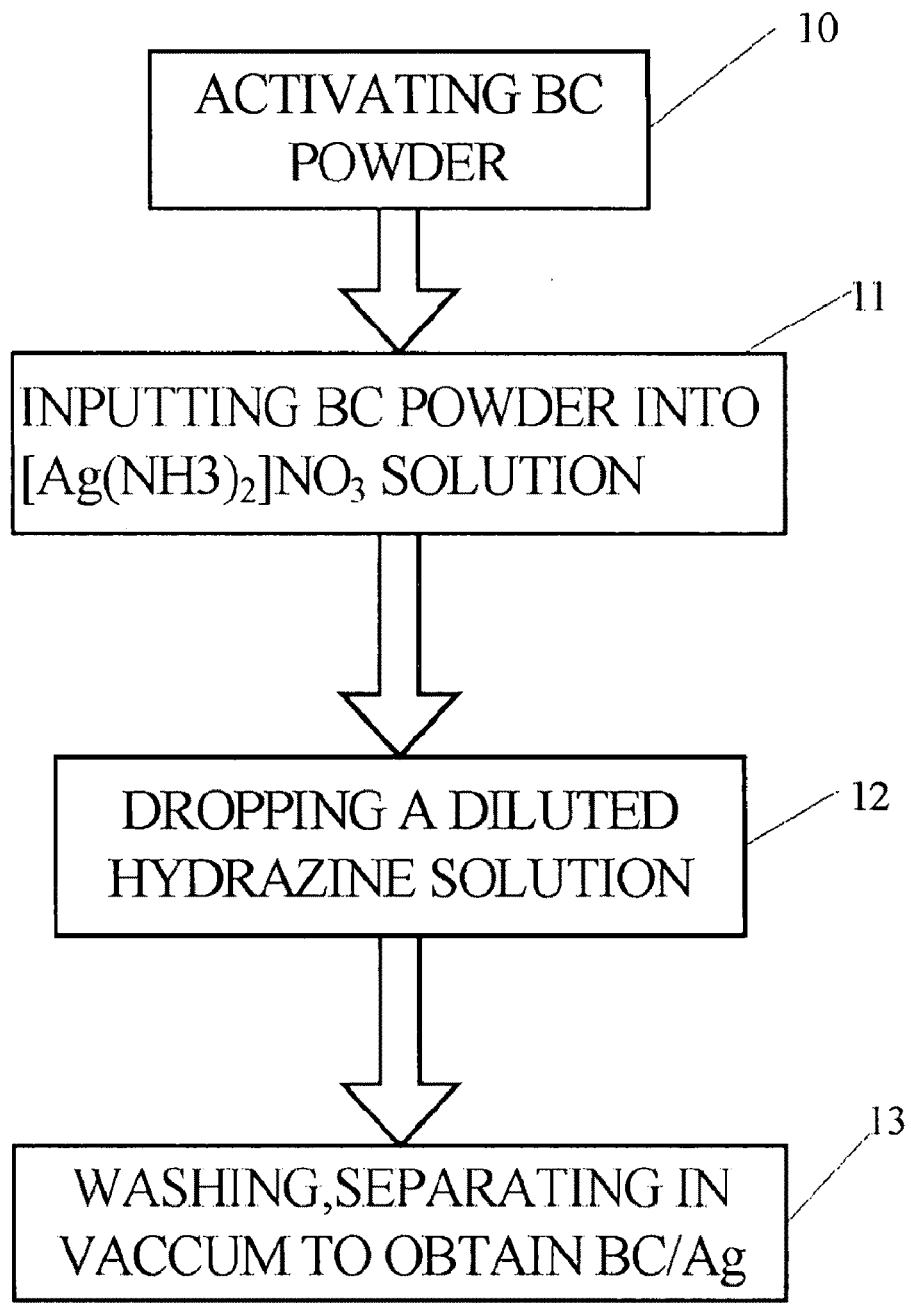
FIG. 1 shows schematic blocks illustrating a manufacturing method of BC/Ag in accordance with the present invention.

A preferred embodiment of the manufacturing method of BC/Ag is shown in FIG. 1, which includes steps of:

1). Activating BC powder (10): The BC powders (particle size<10 μm, Taiwan Paiho) were activated with surfactant sodium alginate under stirred for 1 h;

2). Inputting the BC powder into a biamminesilver nitrate solution (11): The as-prepared BC powders (2 g) were immersed into 100 mL of biamminesilver nitrate ($[Ag(NH_3)_2]NO_3$) solutions, which were formed by adding 28 wt. % aqueous ammonia into $AgNO_3$ solution at room temperature. The weight ratio between BC and $AgNO_3$ approximately equal to 1:1, 1:2, 1:3, 1:4, 1:5 and 1:6, respectively;

3). Dropping diluted hydrazine solution (12): After stirring for 1 h, dilute aqueous solutions of hydrazine monohydrate were separately prepared and were introduced to the BC-$AgNO_3$ solutions in appropriate quantities (molar ratio 1:1 with respect to silver nitrate) by a syringe;

4). Washing, separating and drying in vacuum to obtain silver-supporting bamboo charcoal (BC/Ag) (13): Stirring was continued under inert atmosphere at room temperature for another 4 h. The BC/Ag particles were separated and washed with deionized water and ethanol, then dried in vacuum at 60° C. for overnight; and 5). Marking: The samples were designated BC/Ag-1, BC/Ag-2, BC/Ag-3, BC/Ag-4, BC/Ag-5 and BC/Ag-6 respectively, i.e. the BC/Ag composites, in accordance with the weight ratio of the BC powder and the silver nitrate in 1:1, 1:2, 1:3, 1:4, 1:5 or 1:6. In other words, the weight ratios of the silver are 26% (BC/Ag-1), 29% (BC/Ag-2), 34% (BC/Ag-3), 48% (BC/Ag-4), 57% (BC/Ag-5), and 75% (BC/Ag-6).

Property Test for the BC/Ag Composites (1). Crystal structures of the BC/Ag composites are analyzed by X-ray diffraction(XRD) with Cu Kα radiation. Average grain sizes (D) of Ag were determined from the XRD peaks with Scherrer's formula. The morphology of composites was observed using a scanning electron microscopy (SEM) and a transmission electron microscopy (TEM) equipped with an energy-dispersive X-ray (EDX) microanalysis system.

(2). Nitrogen adsorption isotherms at 77 K measured on the High-Speed Surface Area & Pore Size Analyzer System, were used to characterize the porous structure of the BC/Ag composites. BET specific surface areas, pore volumes and pore size distribution (PSDs) for the samples studied were obtained from nitrogen adsorption isotherms.

Figure 2:
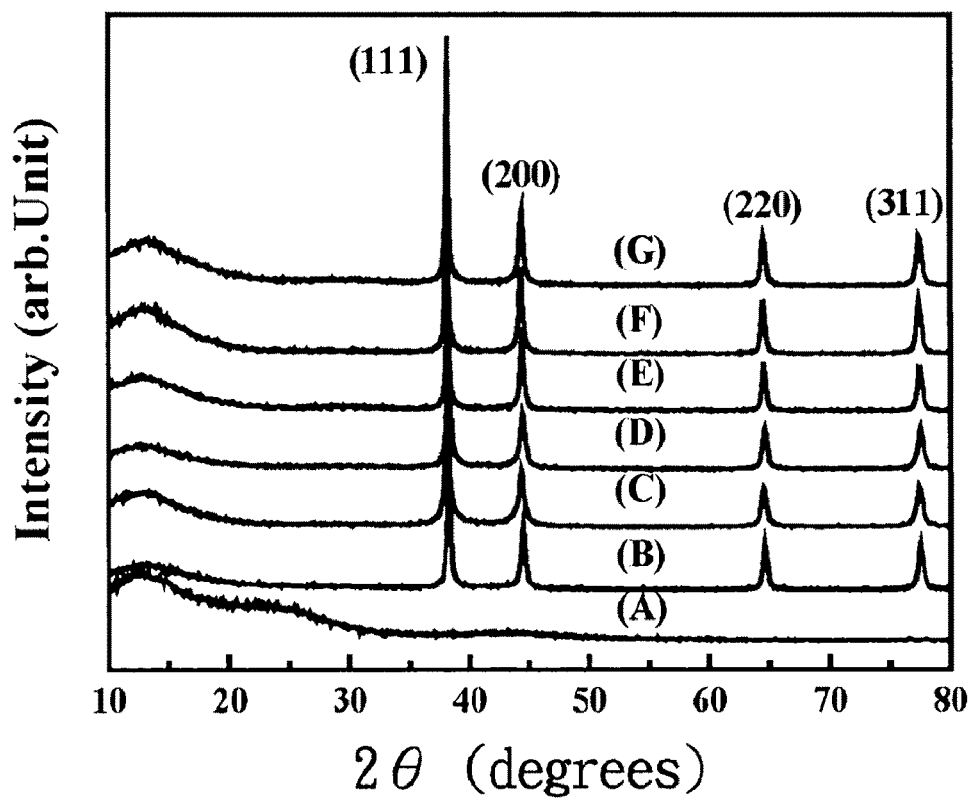
FIG. 2 shows X-ray spectrum diagrams of (A) BC; (B)BC/Ag-1; (C)BC/Ag-2; (D)BC/Ag-3; (E)BC/Ag-4; (F)BC/Ag-55; and (G)BC/Ag-6.
Figure 3:
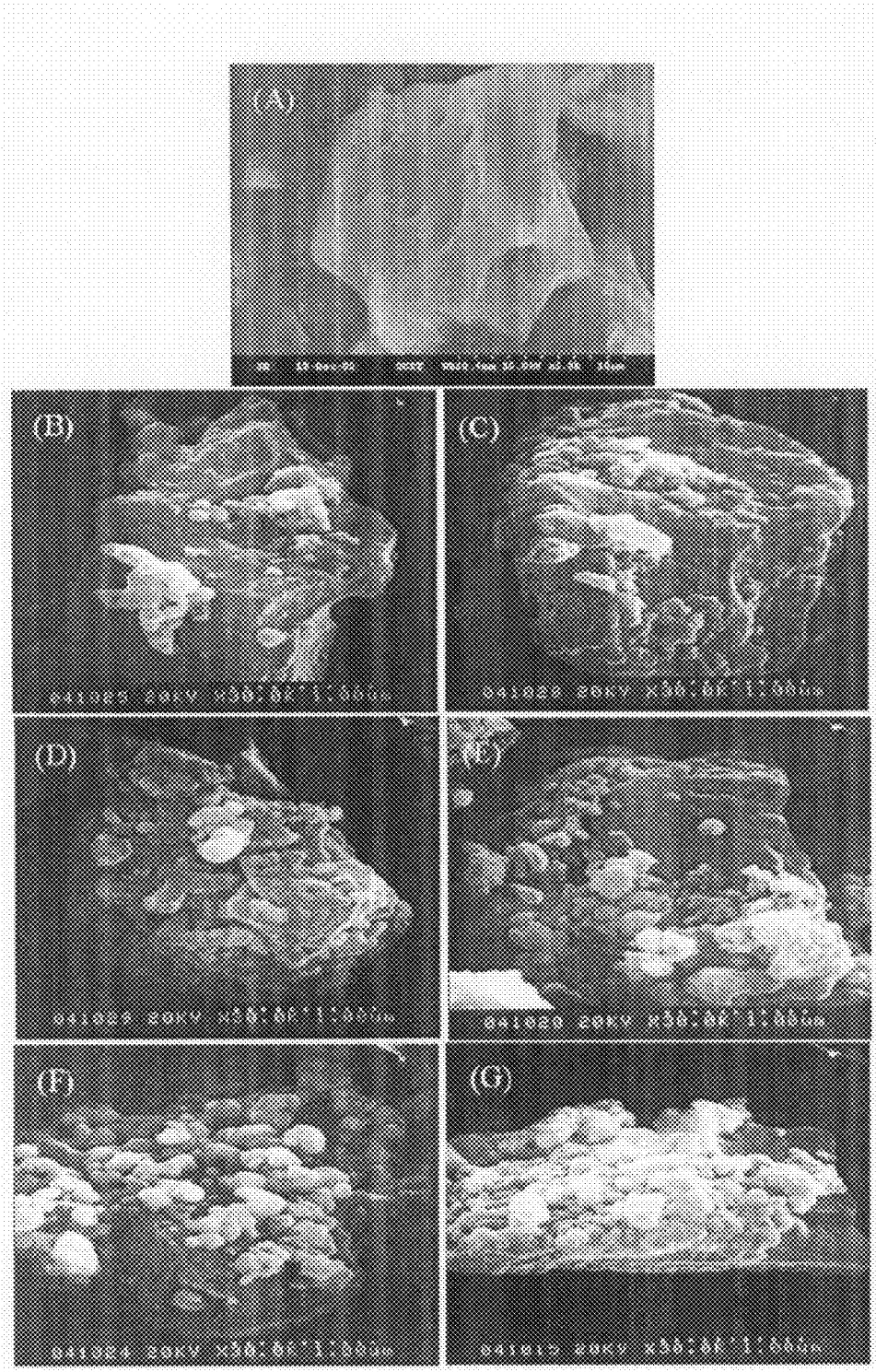
FIG. 3 shows scanning electron microscope (SEM) pictures of (A) BC; (B)BC/Ag-1; (C)BC/Ag-2; (D)BC/Ag-3; (E)BC/Ag-4; (F)BC/Ag-5; and (G)BC/Ag-6.

(3). The concentration of the silver ion released from BC/Ag to the aqueous medium was measured with atomic absorption spectrophotometer Structures and Spectrum Properties of the BC/Ag Composites FIG. 2 shows X-ray diffraction (XRD) patterns of the BC/Ag composites. The weak diffraction peak near 2θ=10° is due to the amorphous phase of BC, its intensity distinctly decreases with increasing Ag content. The XRD of the BC/Ag composites are well in agreement with the literature values of silver nanoparticles. All the prominent peaks at 2θ values of about 38.1, 44.3, 64.5 and 77.4 representing the 111, 200, 220 and 311 Bragg's reflections of face-centered cubic crystalline silver. Furthermore, increase of the amount of $AgNO_3$ in BC induced the obvious enhancement of characteristic peaks of silver, implying the development of larger and highly crystalline silver nanoparticles.

SEM microscopy was used to evaluate the surface morphology of the BC (FIG. 3A) and the BC/Ag composites (FIGS. 3B-G). Pure BC had a porous surface. SEM images of the BC/Ag composites show a little agglomerate and uniformly distributed silver particles. It can be seen that the silver content increases with increasing the initial concentration of $AgNO_3$ solution. The silver particles are of spherical and granular nature and seem to be nanosized, typically in the range of <100 nm.

Figure 4:
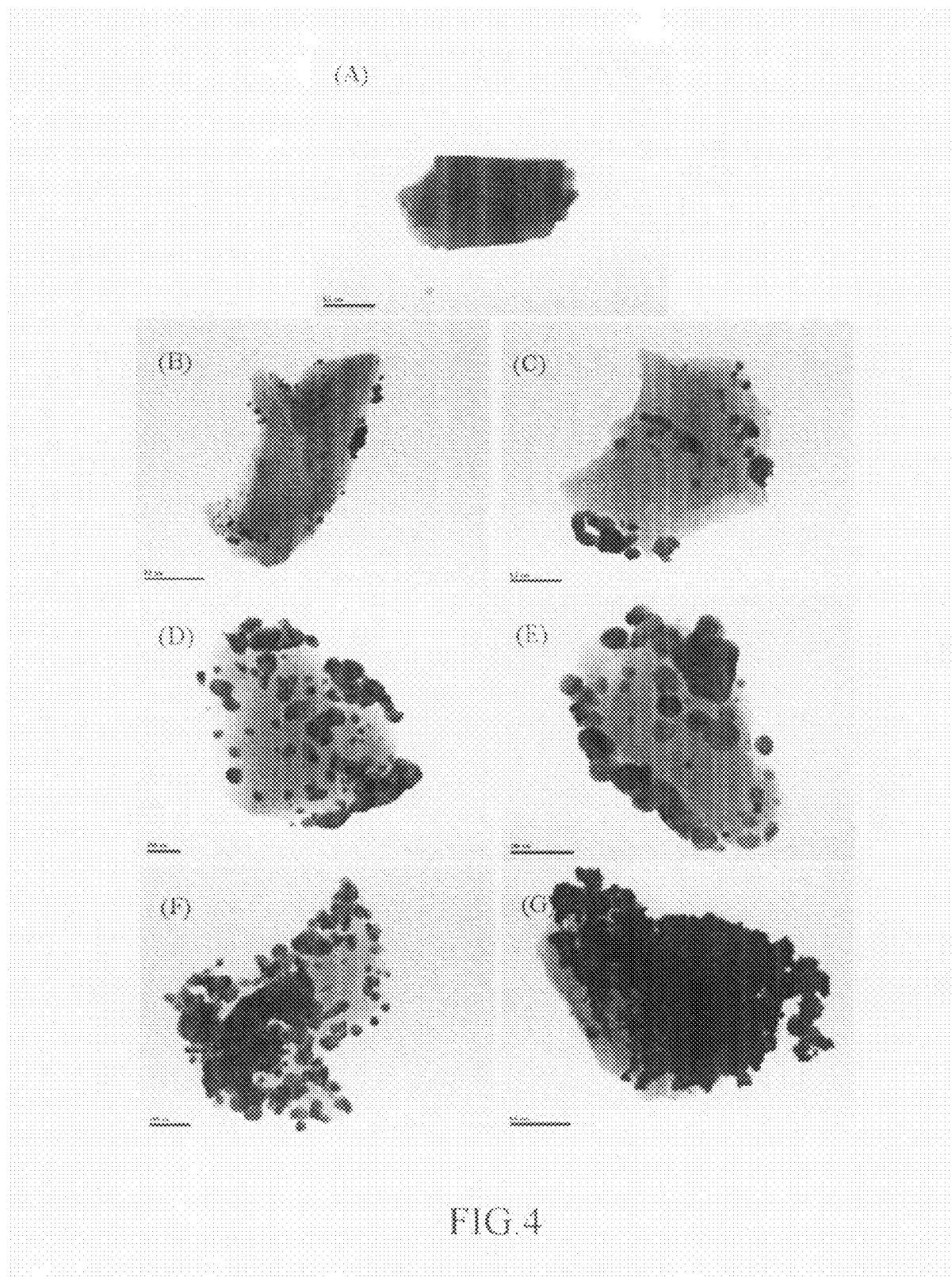
FIG. 4 shows transmission electron microscope (TEM) pictures of (A) BC; (B)BC/Ag-1; (C)BC/Ag-2; (D)BC/Ag-3; (E)BC/Ag-4; (F)BC/Ag-5; and (G)BC/Ag-6.
Figure 5:
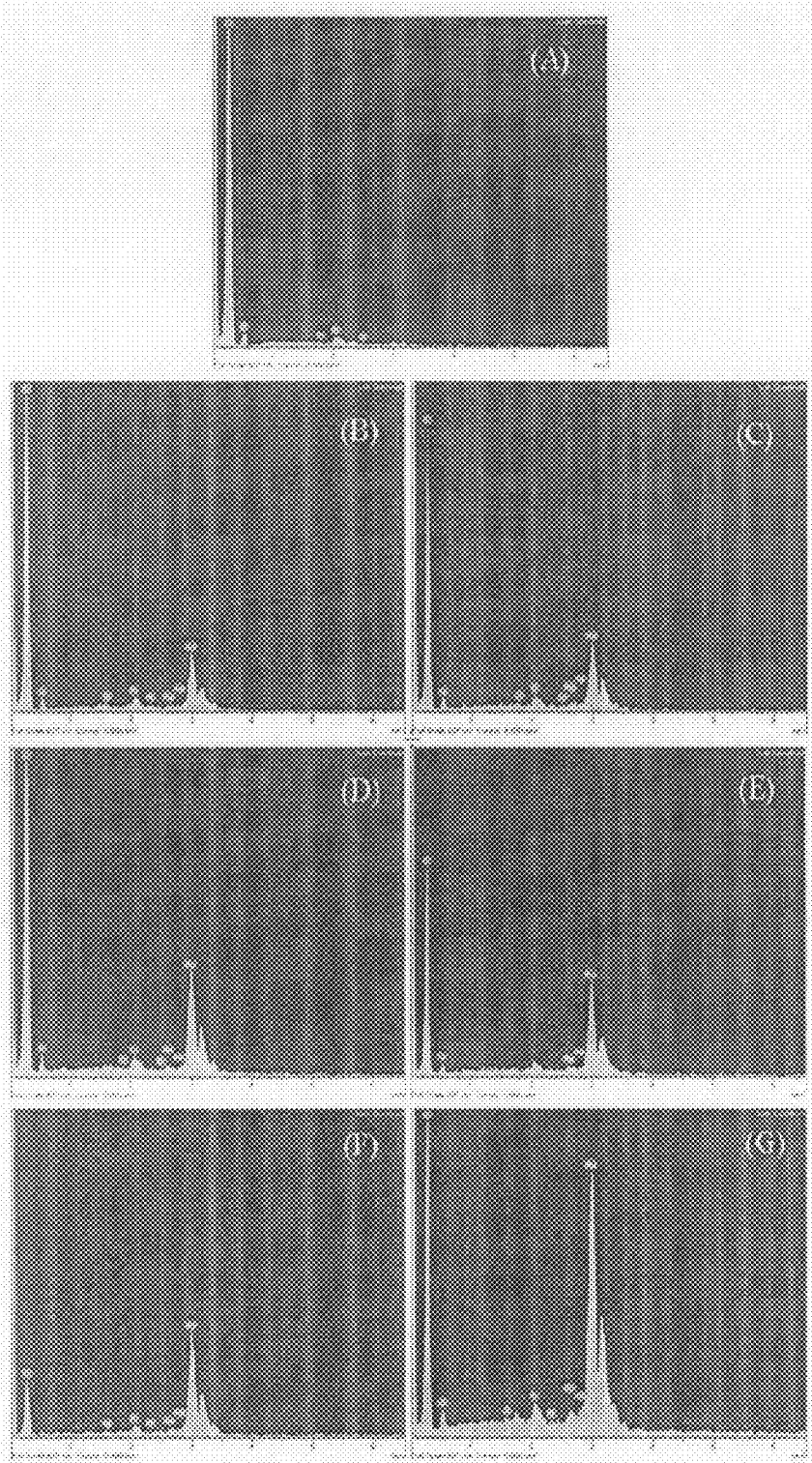
FIG. 5 shows X-ray diffraction (XRD) diagrams of pictures of (A) BC; (B)BC/Ag-1; (C)BC/Ag-2; (D)BC/Ag-3; (E)BC/Ag-4; (F)BC/Ag-5; and (G)BC/Ag-6.
Figure 6:
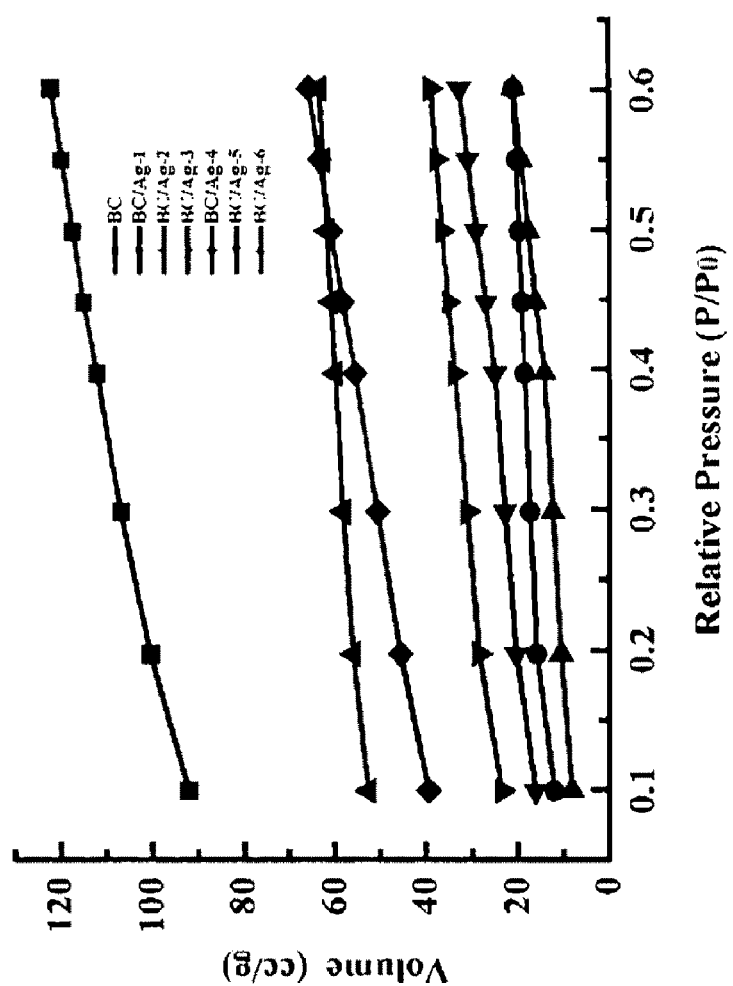
FIG. 6 shows nitrogen adsorption isotherms for only the BC/Ag composites in comparison with those for pure BC.
Figure 7:
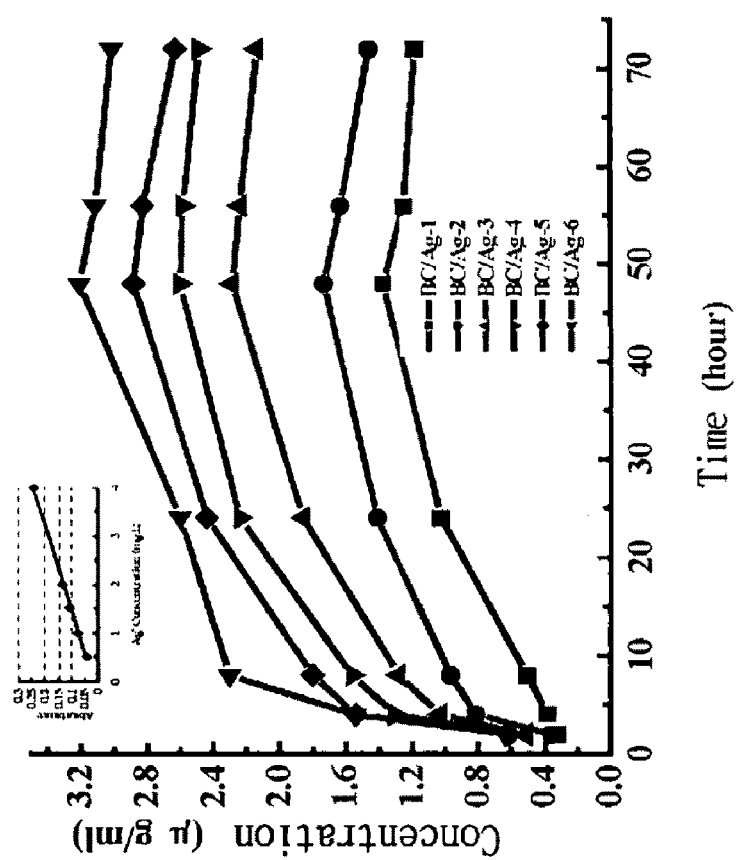
FIG. 7 gives a picture about the time dependency and concentration dependency of the silver ion release for different silver concentrations in the composites.

TEM photographs were used to investigate the particle size and size distribution of silver deposited on the BC surface. As shown in FIG. 4, ultra-fine and aggregated silver particles were homogeneously distributed on the surface of the BC. The BC/Ag composites, on the whole, had a wide range silver particle size distribution from 20 nm to 200 nm. This agreed with the XRD results. The surface composition of BC/Ag composites was qualitatively determined with EDX. It shows that atomic concentration ratios of Ag to C are 86.24/0, 63.39/26.09, 61.30/28.79, 56.43/33.78, 45.43/47.95, 33.59/57.35 and 20.53/74.54, respectively (FIG. 5 and Table 1). Therefore, it can be assumed that Ag nanoparticles are deposited on the surface of the BC particles. FIG. 6 shows nitrogen adsorption isotherms for only the BC/Ag composites in comparison with those for pure BC. The total amount of nitrogen adsorbed increased with increasing activation time. However, all isotherms at higher relative pressures exhibited an almost flat plateau. This means that the external surface area developed by silver particles is negligible and adsorption occurs mainly in micropores. The specific surface areas and total pore volumes of the BC/Ag composites studied are listed in Table 2 and are in agreement with the results reported by Oya et al. As can be seen in this figure, the amount adsorbed on the BC containing silver is lower than that on the corresponding BC without silver. This is consistent with data shown in FIG. 6 and indicates that silver block the formation of pores. FIG. 7 show relationship curve graph between BET's specific surface areas ($S_{BET}$) the BC/Ag composites and concentration of Ag (wt. %). It can be seen that the silver content increases with decreasing the $S_{BET}$ of BC/Ag composites.

TABLE 1

Elemental analysis results of BC/Ag composites

| Composite | wt % | | | |
|---|---|---|---|---|
| | C | O | Ag | Others |
| BC | 86.24 | 11.11 | 0 | 2.65 |
| BC/Ag-1 | 63.39 | 6.92 | 26.09 | 3.60 |
| BC/Ag-2 | 61.30 | 7.17 | 28.79 | 2.75 |
| BC/Ag-3 | 56.43 | 7.30 | 33.78 | 2.49 |
| BC/Ag-4 | 45.43 | 6.62 | 47.95 | 0 |
| BC/Ag-5 | 33.59 | 5.75 | 57.35 | 3.31 |
| BC/Ag-6 | 20.53 | 0 | 74.54 | 4.93 |

TABLE 2

Pore structure parameters of the BC/Ag composites at 77.35K

| Composite | Specific area ($m^2$/g) | Pore volume (cc/g) | Pore diameter (nm) |
|---|---|---|---|
| BC | 317.22 | 0.07 | 3.39 |
| BC/Ag-1 | 170.48 | 0.03 | 3.42 |
| BC/Ag-2 | 155.68 | 0.07 | 3.40 |
| BC/Ag-3 | 96.52 | 0.04 | 3.40 |
| BC/Ag-4 | 92.76 | 0.01 | 3.34 |
| BC/Ag-5 | 55.74 | 0.02 | 3.42 |
| BC/Ag-6 | 54.19 | 0.01 | 3.34 |

Tests for Antibacterial Properties of the BC/Ag Composites:

*P. aeruginosa*(ATCC 27853), *E. coli*(ATCC 25922), *S. aureus*(ATCC 25923) and *B. subtilis* were used for this study, as both are reference strains used for antibacterial testing. They were abstained from the Food Industry Research and Development Moreover, Methicillin-resistant *S. aureus* (MRSA) and Ciprofloxacin-resistant *P. aeruginosa* (CRPA) were collected from the Tri-service General Hospital (Taipei, Taiwan) and all bacteria were stored in Nutrient broth (Difco aboratories, USA) with 15% glycerol (vol/vol) at −70° C. and used in culturing. Stock solutions of test compounds were diluted in Mueller Hinton medium (Difco) immediately before use. The strains were cultured on nutrient agar and incubated aerobically at 37° C. overnight. The qualitative test process was described as follows: 10 mg of the BC/Ag composite powders were fill into the disc (external diameter: 0.6 cm) mixed with deionizer water. After training for 24 h at 37° C., determine their zone of inhibition of microorganisms. To further study the minimum inhibitory concentrations (MIC) of the composites against these microbes. Tubes containing 5 mL Mueller-Hinton broth (MHB) with 10-fold dilutions of the BC/Ag composites ranging from 0.3 mg/L to 0.3 g/L were inoculated with $10^7$ colony-forming units per mL (cfu/mL) of the test organism. The inoculated tubes were then incubated at 37° C. for 18 h. After incubation, tubes were examined without shaking for visible turbidity, the MIC was determined as the lowest dilution of the composites that produced no visible turbidity FIG. 7 gives a picture about the time dependency and concentration dependency of the silver ion release for different silver concentrations in the composites. The data of the $Ag^+$ is related to the release of 1 g of the BC/Ag composites to a 2 L aqueous environment. It can be seen that after an initial increase the $Ag^+$ release shows a minimum towards between hour 8 and 24. However, the $Ag^+$ release increases after the 24th hour for those composites having higher silver content. This result can be explained by the change of the rate of water diffusion and the consequent physical changes to the samples associated with the water diffusion.

Figure 8:
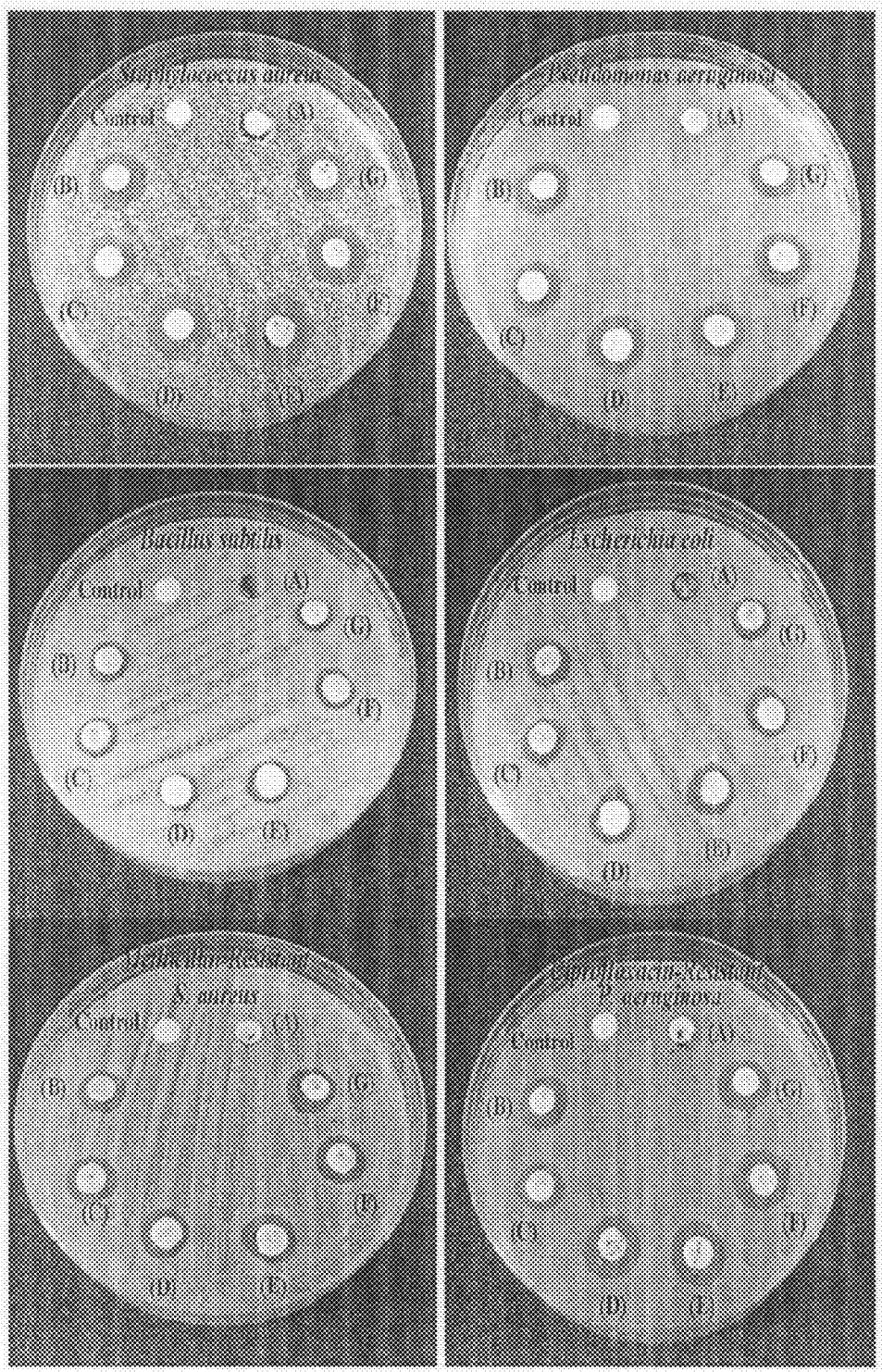
FIG. 8 detail the relative retention of activity (zone of inhibition) of BC and BC/Ag composites against these microbes (A) BC; (B)BC/Ag-1; (C)BC/Ag-2; (D)BC/Ag-3; (E)BC/Ag-4; (F)BC/Ag-5; and (G)BC/Ag-6.

FIG. 8 and Table 3 detail the relative retention of activity (zone of inhibition) of BC and BC/Ag composites against these microbes. After 24 h of incubation, the zones of inhibition of BC/Ag composites against these microbes ranged from 13.0 to 15.0 mm, 11.0 to 12.0 mm, 11.0 to 12.0 mm, 12.0 to 13.0 mm, 10.0 to 11.0 mm, 10.0 to 11.0 mm, and from 9.0 to 10.0 mm, respectively, whereas the BC did not show any zone of inhibition against these microbes.

TABLE 3

Zone of inhibition of bacteria tested against the BC/Ag composites (mm)

| Species | BC (A) | BC/Ag-1 (B) | BC/Ag-2 (C) | BC/Ag-3 (D) | BC/Ag-4 (E) | BC/Ag-5 (F) | BC/Ag-6 (G) |
|---|---|---|---|---|---|---|---|
| S. aureus | 0 | 13 | 13 | 13 | 15 | 15 | 15 |
| MRSA | 0 | 11 | 11 | 11 | 12 | 12 | 12 |
| P. aeruginosa | 0 | 11 | 11 | 12 | 12 | 12 | 12 |
| CRPA | 0 | 12 | 12 | 12 | 13 | 13 | 13 |
| B. subtilis | 0 | 9 | 9 | 9 | 10 | 10 | 10 |
| E. coli | 0 | 10 | 10 | 11 | 11 | 11 | 11 |

Additionally, as shown in FIG. 9, the BC/Ag composites were applied to personal sanitary bag (9A), OK bandage (9B), ointments (9D) to wound, and tablets (9C) to purify and sterilize water. Other application of the BC/Ag composites are illustrated as below.

A manufacturing method of ointment with the BC/Ag composites comprises steps of: inputting 5 g of paraffin[0] wax white in a 300 ml beaker, melting the paraffin in water bath at 80° C., adding 95 g of petroleum white that is melt at 90° C., terminating heating and stirring until solidifies to obtain a white ointment, preparing 1 g of the BC/Ag composites and 1 g of mineral oil to be ground together on a glass disk to become a smooth paste, and mixing the smooth paste with 8 g of the white ointment to obtain the ointment product with the BC/Ag composites.

A manufacturing method of a personal sanitary bag comprises steps of: stuffing 0.5 g of the BC/Ag composites into a bag and sealing the bag to obtain the personal sanitary bag.

A manufacturing, method of an OK bandage comprises a step of; embedding the BC/Ag powder within yarns of a bandage.

A manufacturing method of a tablet comprises steps of grinding 0.25 g of the BC/Ag composites with 0.018 g of starch, 0.06 g of lactose and 0.002 g of magnesium stearate into a powder mixture and punching the powder mixture into tablet with 1.3 cm diameter by a tabletting machine with 3000 psi to obtain the tablet product.

CONCLUSIONS

In this work, porous bamboo charcoal has been successfully adopted as novel supports for immobilization of silver nanoparticles by a chemical reduction method and the antibacterial efficacy of the BC/Ag composites were investigated. SEM and TEM revealed that the silver particles of 20-200 nm in diameter were uniformly distributed on BC matrix. BC/Ag composites have the potential antibacterial efficacy by virtue of their ability to release silver ions. Composites containing higher concentrations of the silver powder possess a higher release when the storage time exceeds 24 hours. The results of antibacterial tests for the BC/Ag with varying silver contents showed that the BC did not show antibacterial effect, but all BC/Ag composites exhibited strong antibacterial properties against these microbes.

Although this invention has been described in its preferred form with a certain degree of particularity, it is understood that the present invention of the preferred form has been made only by way of example and that numerous changes in the details of construction and the combination and arrangement of parts any be resorted to without departing from the spirit and scope of the invention.

What is claimed is:

1. A manufacturing method of silver-supporting bamboo charcoal (BC/Ag) comprising steps of:
   mixing bamboo charcoal powder with a surfactant and alginic acid sodium salt to activate the bamboo charcoal powder;
   inputting activated bamboo charcoal powder into ammoniacal silver nitrate solution ($[Ag(NH_3)2NO_3(aq)]$) at room temperature to compose a mixture, wherein the ammoniacal silver nitrate solution is made by mixing 28 wt % ammonia and 72 wt % silver nitrate, wherein weight ratio of the bamboo charcoal powder and the silver nitrate molecules in the ammoniacal silver nitrate solution has a range of 1:1 to 1:6;
   dropping a diluted hydrazine solution into the mixture and keeping the mixture reacting at room temperature and nitrogen atmosphere;
   washing with deionized water and ethanol; and
   drying to obtain silver supporting bamboo charcoal (BC/Ag) particles.

2. The manufacturing method as claimed in claim 1, wherein the silver-supporting bamboo charcoal (BC/Ag) particles has diameters less than 10 μm.

3. The manufacturing method as claimed in claim 1, wherein a weight ratio of the diluted hydrazine solution and the silver nitrate molecules in the ammoniacal silver nitrate solution is 1:1.

4. The manufacturing method as claimed in claim 1, wherein
   mixing the bamboo charcoal powder with the surfactant and the alginic acid sodium salt to stir for 1 hour to activate the bamboo powder;
   inputting 2 g of the activated bamboo charcoal powder into 100 ml of ammoniacal silver nitrate solution ($[Ag(NH_3)_2]NO_3(aq)$) in room temperature to compose the mixture and stirring the mixture for 1 hour;
   dropping the diluted hydrazine solution into the mixture and keeping the mixture reacting for 4 hours in room temperature and nitrogen atmosphere;
   washing with the deionized water and the ethanol; and
   drying in vacuum at 60° C. to obtain the silver-supporting bamboo charcoal (BC/Ag) particles.

* * * * *